United States Patent
Lemann et al.

(10) Patent No.: US 6,346,237 B2
(45) Date of Patent: *Feb. 12, 2002

(54) COSMETIC COMPOSITIONS COMPRISING LIQUID CRYSTAL COLORING AGENTS AND THEIR USE

(75) Inventors: Patricia Lemann, Chatillon; Myriam Mellul, L'Hay-Les-Roses; Annick Collette, Choisy le Roi; Isabelle Bara, Paris, all of (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/348,678

(22) Filed: Jul. 6, 1999

Related U.S. Application Data

(63) Continuation of application No. 08/886,449, filed on Jul. 1, 1997.

(30) Foreign Application Priority Data

Jul. 2, 1996 (FR) .............................................. 96-08221

(51) Int. Cl.⁷ .......................... A61K 7/04; A61K 7/021; A61K 31/74; A61K 9/14
(52) U.S. Cl. .......................... 424/61; 424/401; 424/63; 424/78.03; 424/489
(58) Field of Search ........................... 424/401, 63, 61, 424/78.03, 489

(56) References Cited

U.S. PATENT DOCUMENTS

| | | | |
|---|---|---|---|
| 4,301,023 A | 11/1981 | Schuberth et al. | |
| 5,242,617 A | * 9/1993 | Metzger et al. | .......... 252/299.5 |
| 5,362,315 A | 11/1994 | Mueller-Rees et al. | |
| 5,658,575 A | * 8/1997 | Ribier et al. | ................. 424/401 |
| 5,690,916 A | 11/1997 | Kimura | |
| 5,851,277 A | 12/1998 | Mueller-Rees et al. | |
| 5,851,604 A | * 12/1998 | Müller-Rees et al. | .......... 428/1 |

FOREIGN PATENT DOCUMENTS

| | | |
|---|---|---|
| DE | 4240743 | 6/1994 |
| EP | 0686674 | 12/1995 |
| WO | WO 90/02161 | 3/1990 |
| WO | WO 94/22976 | * 10/1994 |
| WO | WO 95/08786 | * 3/1995 |

OTHER PUBLICATIONS

J.–P. Caquet et al., "*Les Cristaux Liquides dans les Cosmétiques*," Parfums Cosmetiques Aromes, 6037, No. 91, pp. 77–82 (1990).

Derwent Abstract of Japanese Patent Appln. No. 88–268268.

Derwent Abstract of Japanese Patent Appln. No. 89–43255.

Derwent Abstract of EP 0686674.

* cited by examiner

*Primary Examiner*—Thurman K. Page
*Assistant Examiner*—S. Howard
(74) *Attorney, Agent, or Firm*—Finnegan, Henderson, Farabow, Garrett & Dunner, L.L.P.

(57) ABSTRACT

The present invention relates to a cosmetic composition, more particularly a make-up cosmetic composition, comprising a liquid crystal (LC) coloring agent which makes it possible to obtain novel coloring effects, in particular to obtain distinct colors depending on the incidence of the light and the angle of observation.

37 Claims, No Drawings

COSMETIC COMPOSITIONS COMPRISING LIQUID CRYSTAL COLORING AGENTS AND THEIR USE

This is a continuation of application Ser. No. 08/886,449, filed Jul. 1, 1997, and claims the benefits of same application, which is incorporated herein by reference.

The present invention relates to a new cosmetic composition, in particular a make-up cosmetic composition, comprising a colouring agent of liquid crystal type (hereinafter LC colouring agent), which makes it possible to obtain novel colouring effects, in particular to obtain distinct colours according to the incidence of the light and the angle of observation.

Make-up compositions, such as loose or compact powders, foundations, blushers, eye-shadows, lipsticks or nail varnishes, are composed of an appropriate vehicle and of different colouring agents intended to confer a certain colour on the compositions before and/or after their application on the skin, mucous membranes (in particular the lips) or superficial body growths.

A fairly limited range of colouring agents is currently used to create colours, in particular pigments such as lakes, inorganic pigments or pearlescent pigments.

Lakes make it possible to obtain vivid colours but, for the most part, are unstable to light, to temperature and to pH. Some also exhibit the disadvantage of staining the skin in an unsightly way after application, by releasing the dye.

In contrast, inorganic pigments, in particular inorganic oxides, are very stable but give rather dull and pale colours.

In order to obtain coloured effects, it is possible to employ pearlescent pigments of varied but never intense colours which make it possible to obtain iridescent but generally fairly weak effects.

The present invention thus relates to a new cosmetic composition comprising a cosmetically acceptable support and an LC colouring agent capable of producing a colour within a range of hues, said color existing between at least two specific colors and varying as a function of the incidence of the light and the angle of observation. The colouring agent is chosen from linear or cyclic polymers onto which mesomorphic groups are grafted. The LC colouring agent may be used alone or in combination with at least one non-LC colouring agent.

Colour is preferably understood to mean according to the invention any colour in the visible spectrum. The specific colours of the colouring agents are preferably transmitted in visible light.

Colouring agent is understood to mean a material intended to give a lasting colouring to a material or composition. It is possible to distinguish, on the one hand, dyes which are essentially soluble in their medium of use and, on the other hand, pigments composed of fine particles which, in contrast to dyes, are insoluble in their medium of use.

These LC colouring agents are described in particular in Patents and Patent Applications EP 29 162, EP 66 137, EP 60 335, DE 37 32 115, EP 333 022, EP 358 208, EP 385 376, EP 404 140, EP 424 259, EP 431 466, EP 446 912, EP 446 183, EP 545 409, WO 94/09086, DE 43 28 761, EP 635 749, EP 661 287, EP 709 445, JP 60 148 173, JP 07 278 308, US 5 364 557, GB 2 280 681, GB 2 282 145, GB 2 276 883, GB 2 282 146, WO 95/32247, WO 95/32248, EP 601 483, EP 626 386, EP 686 674 and EP 711 780, which are incorporated here by reference.

The LC colouring agents are more particularly silicones or cellulose ethers, onto which are grafted mesomorphic groups, which can be employed alone and/or coated onto inert supports, such as micas, and/or combined with other non-LC colouring agents.

The mesomorphic groups are generally groups of formula

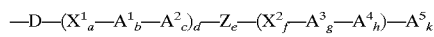

in which

D represents a $C_1$–$C_{20}$ alkylene residue, optionally substituted by one or a number of halogens, for which one or a number of the non-neighbouring methylene units can be replaced by an $X^1$ group, $X^1$ and $X^2$ independently represent —O—, —COO—, —CONH—, —CO—, —S—, —C≡C—, —CH=CH—, —CH$_2$—CH$_2$—, —CH=N—, —N=N— or —N=N(O)— divalent radicals, $A^1$, $A^2$, $A^3$ and $A^4$ independently represent optionally substituted 1,4-phenylene, 1,4-cyclohexylene, arylene, heteroarylene or cycloalkylene divalent radicals, Z independently represents divalent to tetravalent radicals, benzene-1,4-cyclohexane or benzene-1,3-cyclopentane, $A^5$ independently represents a saturated or unsaturated alkyl, alkoxy or cycloalkyl radical having 1 to 16 carbon atoms, a steroidal radical, a halogen, a hydrogen atom or a hydroxyl, nitrile or trialkylsilyloxy radical, a, b, c, d, f, g, h, i and k independently represent an integer of between 0 and 3, e represents 0 or 1, with the sum a+b+c+d+e+f+g+h+i+k being greater than or equal to 2 and the sum d+i being less than or equal to 4, it being understood that this mesomorphic group does not comprise a peroxide radical.

In particular, the LC colouring agents of the invention can be provided in the form of amorphous white powders and be similar to "pigments". The colour and/or the colouring effect only appears on spreading the composition which contains them, in particular as a function of the colour of the substrate on which they are spread and/or the presence of possible associated non-LC colouring agents.

The LC "pigments" can in particular be composed of oriented substances with three-dimensional crosslinking comprising a mesomorphic group, in particular as defined above, which can comprise at least one polymerizable group, having a mean thickness of between 1 and 100 µm and a mean diameter of between 1 and 10,000 µm. These LC pigments with a mesomorphic structure can be prepared by crosslinking after orientation, after the possible addition of non-LC pigments, and then milling to the desired particle size.

A particularly preferred form of LC colouring agent in accordance with the invention comprises cyclic polyorganosiloxanes grafted with cholesterol and biphenyl groups. They are described in particular in the article by H. J. Eberle, A. Miller and F. H. Kreuzer, Liquid Crystals, 1989, Vol. 5, No. 3, 907–916, in the article by J. Pinsl, Chr. Braüchie and F. H. Kreuzer, Journal of Molecular Electronics, Vol. 39–13 (1987) and U.S. Pat. No. 4,410,570.

They are more particularly still chosen from cyclomethicones grafted with cholesterol and biphenyl groups with the following formula:

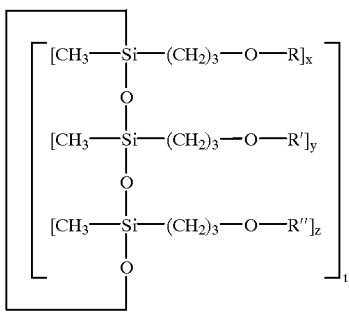

(I)

in which:
$0 \leq x \leq 1$ (preferably 1), $0 \leq y \leq 1$ (preferably 1) and $0 \leq z \leq 1$ (preferably 1) with $x+y+z \neq 0$ and $3 \leq t \leq 10$;
R denotes a group of the following formula:

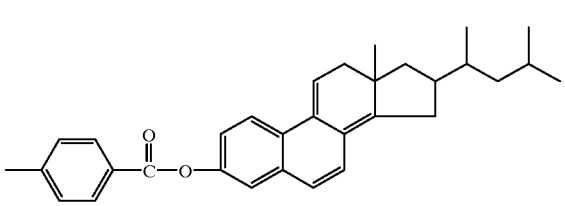

(II)

R' denotes a group of the following formula:

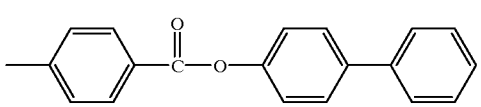

(III)

and R" denotes a group of the following formula:

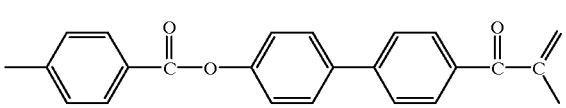

(IV)

These compounds are generally provided in the form of amorphous white powders. The colour and/or the colouring effect are within a range of hues that corresponds to at least two specific colours and varies as a function of the incidence of the light and of the angle of observation. The colour and/or the colouring effect only appear on spreading the composition that contains them, in particular as a function of the colour of the substrate on which it is spread and/or of the presence of possible associated non-LC colouring agents.

Mention may be made, as examples of LC colouring agents corresponding to this definition, of in particular the "LC pigments" sold by the company Wacker under the names SLM 41101 (Blue/Green), SLM 41102 (Red/Gold) and SLM 41103 (Yellow/Green).

The cosmetic compositions according to the invention are essentially those relating to making up the face, that is to say eye-shadows, eye-liners, mascaras, powders, foundations, blushers, tinted creams, lipsticks or concealer sticks, but also making up the hair, in particular gels, creams or mousses for the hair, and making up the nails, in particular anhydrous and aqueous nail varnishes.

Non-LC colouring agent is understood to mean non-LC dyes and/or non-LC pigments usual in the art.

Pigments are natural or synthetic substances composed of fine particles which, in contrast to dyes, are insoluble in their medium of use, the main function of which is to give a colouring. Different types of pigments are distinguished: inorganic pigments, organic pigments, lakes or pearlescent pigments. Lakes are dyes adsorbed on insoluble particles, the combination remaining essentially insoluble in the medium of use. Pearlescent pigments are natural or synthetic substances which scatter and reflect light to give an iridescent or bright effect.

Mention may be made, among dyes, of natural organic dyes, such as cochineal carmine (Cl 75 470), or synthetic organic dyes, such as haloacid, azo or anthraquinone dyes. Mention may also be made of inorganic dyes, such as copper sulphate.

Mention may be made, among inorganic pigments, of metal oxides, in particular zirconium, cerium, zinc or chromium oxides (Cl 77 288), titanium dioxide (Cl 77 891), black, yellow, red and brown iron oxides (Cl 77 499, Cl 77 492 or Cl 77 491), manganese violet (Cl 77 742), ultramarine blue (Cl 77 007), iron blue (Cl 77 510), chromium hydrate (Cl 77 289), silver powder or aluminium powder.

Mention may be made, among organic pigments, of carbon black (Cl 77 266) or D & C Red 36.

Lakes are generally composed of metal salts (in particular Al, Zr, Ca or Na) of organic dyes adsorbed on particles, for example of alumina, of barium sulphate, of colophony, and the like. Mention may be made, among lakes, of those known under the names: D & C Red 21 (Cl 45 380), D & C Orange 5 (Cl 45 370), D & C Red 27 (Cl 45 410), D & C Orange 10 (Cl 45 425), D & C Red 3 (Cl 45 430), D & C Red 7 (Cl 15 850:1), D & C Red 4 (Cl 15 510), D & C Red 33 (Cl 17 200), D & C Yellow 5(Cl 19 140), D & C Yellow 6 (Cl 15 985), D & C Green 5 (Cl 61 570), D & C Yellow 10 (Cl 77 002), D & C Green 3 (Cl 42 053), D & C Blue 1 (Cl 42 090).

Mention may be made, among pearlescent pigments, of bismuth oxychloride or mica covered with titanium oxide, with iron oxide or with natural pigments, for example coloured titanium dioxidecoated mica.

In the compositions according to the invention, the total amount of LC and non-LC colouring agents is preferably between approximately 0.01 and approximately 60% by weight with respect to the total weight of the composition, in particular between approximately 0.1 and 30% by weight, more particularly between 1 and 20% by weight.

When the composition comprises non-LC colouring agents, the LC colouring agentsinon-LC colouring agents ratio by weight is advantageously between 20/1 and 1/20, preferably between 10/1 and 1/10, more preferentially between 5/1 and 1/5.

The cosmetic compositions according to the invention can furthermore contain additional fillers usual in cosmetics.

Fillers are natural or synthetic materials, the main function of which is to modify the physicochemical (rheological, mechanical, optical) and/or cosmetic properties of a composition. Fillers are colourless or more or less white in the dry state. They are virtually transparent when dispersed in a binder.

Mention may be made, among fillers, of talc, which is a hydrated magnesium silicate, used in the form of particles with dimensions generally of less than 40 $\mu$m; talc possesses moisture-absorbing properties and is used especially because of its smooth feel; micas, which are aluminosilicates of varied compositions which are provided in the form of flakes having dimensions of 2 to 200 µm, preferably of 5 to 70 µm, and a thickness of 0.1 to 5 µm, preferably of 0.2 to 3 µm; micas can be of natural origin (muscovite, margarite, roscoelite, lepidolite or biotite, for example) or of synthetic origin; they are generally transparent and make it possible to confer a satin appearance on the skin; starch, in particular rice starch; silica; kaolin, which is a hydrated aluminium silicate, which is provided in the form of particles with an isotropic shape having dimensions generally of less than 30 µm and which has good absorption properties with respect to fatty substances; Nylon® (in particular Orgasol) and polyethylene powders; Teflon®; boron nitride; copolymer microspheres, such as Expancel® (Nobel Industrie) or polytrap® (Dow Coming), and silicone resin microbeads (Tospearls® from Toshiba, for example); precipitated calcium carbonate which, in the form of particles with dimensions of less than 10 µm, has a smooth feel and makes it possible to obtain a matt appearance; magnesium carbonate or hydrocarbonate which has in particular perfume-fixing properties; metal soaps derived from organic carboxylic acids having from 8 to 22 carbon atoms, preferably from 12 to 18 carbon atoms, for example zinc, magnesium or lithium stearate, zinc laurate, magnesium myristate, and the like; these soaps, generally present in the form of particles having dimensions of less than 10 µm, have a smooth feel and facilitate adhesion of the powder to the skin.

According to the type of formulation, the fillers can represent from 0.01 to 90% by weight of the composition.

When the composition according to the invention does not contain other non-LC colouring agents, a product is then obtained which is colourless or which has a slight iridescent effect.

This composition can be employed in different ways, depending on whether the composition according to the invention contains or does not contain other non-LC colouring agents.

Use may be made of a composition according to the invention which does not contain other non-LC colouring agents as top coat, that is to say above a make-up base exhibiting a specific colour, preferably a dark colour. The application of the composition according to the invention makes it possible to produce a new very vivid lasting colour identical to or different from the specific colour of the make-up base. This new colour is very intense and very bright and luminous, with an improved intensity, brightness and/or luminosity with respect to the specific colour of the make-up base. Such an effect is distinguished from the effects generally obtained with the usual pigments and/or pearlescent pigments of the art.

When the colour of the make-up base is essentially similar to one of the specific colours of the LC colouring agent, this LC colouring agent acts as colour-reinforcing agent.

When the colour of the make-up base is different from the specific colours of the LC colouring agent, the latter acts as colour-modulating agent.

Finally, when the make-up base is black, the black disappears and only the specific colours of the LC colouring agent are revealed.

The make-up film obtained after application exhibits distinct colours according to the orientation of the incident light and of the angle of observation. It is possible, for example, to obtain a colour within the range corresponding to the blue/green or red/green pair, depending on the LC colouring agent employed and the specific colour of the make-up base. These colour effects are accompanied by a very luminous glittering effect. In certain cases, it is even possible to distinguish intermediate hues.

It is also possible to employ the composition according to the invention, which does not contain other non-LC colouring agents, directly on the skin or superficial body growths.

When this composition according to the invention is applied directly on the hair or eyelashes, novel colouring effects are obtained according to the colour of the hair or eyelashes on which the composition is applied. Thus, on light hair, very intense and sparkling highlights are obtained. These highlights correspond to the pair of specific to colours of the LC colouring agent, which are not strongly distinguished. On dark hair or eyelashes, very distinct colours are obtained according to the orientation of the incident light and of the angle of observation; these colours are within the range of hues corresponding to the pair of specific colours of the LC colouring agent. Depending on the LC colouring agent employed, it is possible to obtain combinations of colours, such as blue/green or gold/blue, and the like.

When the composition according to the invention is applied directly on the face, a specific effect of uniformization of the complexion is obtained, which effect makes it possible in particular to correct red blotches on the skin (for example by selecting an LC colouring agent combining the green/blue colours).

When the composition according to the invention contains other non-LC colouring agents, in particular other non-LC pigments, It is possible to obtain distinct effects by the selection of the LC colouring agents associated with specific pairs of colours.

Thus, when an LC colouring agent is employed in which one of the colours of the pair of specific colours is essentially similar to the colour of the non-LC colouring agent (or of the combination of non-LC colouring agents) present in the composition according to the invention, the LC colouring agent reinforces and intensifies the said colour, while producing a change in colour according to the incidence of the light and the angle of observation.

In contrast, when an LC colouring agent is employed in which the specific colours are different from the colour of the non-LC colouring agent (or of the combination of non-LC colouring agents) present in the composition according to the invention, a new tone of the colour of the non-LC colouring agent (or of the combination of non-LC colouring agents) is obtained, which tone is more or less intense according to the saturation of the said colour. The more saturated the colour under consideration, the more intense the modification in its tonality.

Finally, when an LC colouring agent is employed with a black colouring agent, it is the specific colours of the LC colouring agent which are revealed, the black disappearing.

The present invention thus relates to a cosmetic composition comprising, as colouring agent, the combination of an LC colouring agent as defined above, capable of producing a colour within a range of hues corresponding to at least two colours, and at least one non-LC colouring agent, the colour of which is essentially similar to one of the said specific colours of the LC colouring agent. In this case, the LC colouring agent fulfils the function of colour-reinforcing agent.

The present invention also relates to a cosmetic composition comprising, as colouring agent, the combination of an LC colouring agent as defined above, capable of producing a colour within a range of hues corresponding to at least two specific colours, and at least one non-LC colouring agent, the colour of which is different from the said specific colours of the LC colouring agent. In this case, the LC colouring agent fulfils the function of colour-modulating agent.

The present invention also relates to a cosmetic composition comprising, as colouring agent, the combination of an LC colouring agent as defined above, capable of producing a colour within a range of hues corresponding to at least two specific colours, and a black colouring agent. In this case, it is the specific colours of the LC colouring agent which are revealed, the black disappearing.

The present invention also relates to the use of an LC colouring agent as defined above, in a cosmetic composition which does not contain non-LC colouring agents, as agent for the uniformization of the complexion, for a direct application on the skin or the lips.

The present invention also relates to the use of an LC colouring agent as defined above, in a cosmetic composition which does not contain non-LC colouring agents, as colour-reinforcing agent for a direct application on a make-up base comprising at least one non-LC colouring agent with a colour essentially similar to one of the specific colours of the LC colouring agent.

The present invention also relates to the use of an LC colouring agent as defined above, in a cosmetic composition which does not contain non-LC colouring agents, as colour-modulating agent for a direct application on a make-up base comprising at least one non-LC colouring agent with a colour different from the specific colours of the LC colouring agent.

Finally, the present invention relates to the use of an LC colouring agent as defined above, in a cosmetic composition which does not contain non-LC colouring agents, for a direct application on a make-up base comprising at least one black colouring agent or on brown or black eyelashes or eyebrows.

Agent for the uniformization of the complexion is understood to mean, according to the invention, a compound (or a composition) with the function of reducing and/or correcting coloristic imperfections of the skin, such as colour blemishes, blotchiness, spots, and the like.

Colour-reinforcing agent is understood to mean, according to the invention, a compound (or a composition) which has the function of saturating the colour in question.

Colour-modulating agent is understood to mean, according to the invention, a compound (or a composition) which has the function of modifying the tonality of the said colour (producing a shift in tone). For example, for a red colour with a bluish tone, a red colour with an orangey tone is obtained with an appropriate colour modulator.

Non-LC colouring agent is understood to mean, according to the present invention, any standard non-LC colouring agent employed in cosmetic compositions. When the colour of the composition corresponds to a mixture of a number of non-LC colouring agents, the expression "non-LC colouring agent" also encompasses the said mixtures of non-LC colouring agents. In this case, the expressions "colour essentially similar to one of the specific colours of the LC colouring agent" or "colour different from the specific colours of the LC colouring agent" or "colour substantially corresponding to one of the specific colours of the LC colouring agent" apply to the colour of the said mixture of non-LC colouring agents.

The compositions according to the present invention can in particular be provided in the form of an oil-in-water or water-in-oil emulsion or in the form of a suspension in solvent medium or alternatively in the form of a loose powder or a compact powder or of an anhydrous solid or of an anhydrous paste or alternatively in the gel or mousse form. The procedures for the preparation of these different types of composition are well known to the person skilled in the art.

When they are used in the emulsion form, the compositions according to the invention can contain surface-active agents well known in the state of the art. These surfactants can constitute from 0.01 to 30% by weight with respect to the total weight of the composition.

A particularly preferred implementation comprises the preparation of anionic or non-ionic emulsions by using anionic or non-ionic surface-active agents in proportions preferably of between 2 and 30% by weight with respect to the total weight of the composition.

Mention may in particular be made, among anionic surface-active agents which can be used alone or as a mixture, of alkali metal salts, ammonium salts, amine salts or aminoalcohol salts of the following compounds:

alkyl sulphates, alkyl ether sulphates, alkylamide sulphates and ether sulphates, alkylaryl polyether sulphates or monoglyceride sulphates, alkylsulphonates, alkylamide sulphonates, alkylarylsulphonates, α-olefin sulphonates or paraffin sulphonates, alkyl sulphosuccinates, alkyl ether sulphosuccinates or alkylamide sulphosuccinates, alkyl sulphosuccinamates, alkyl sulphoacetates or alkyl polyglycerol carboxylates, alkyl phosphateslalkyl ether phosphates, acylsarcosinates, alkylpolypeptidates, alkylamidopolypeptidates, acylisethionates or alkyllaurates.

The alkyl or acyl radical in all these compounds generally denotes a chain containing 12 to 18 carbon atoms.

Other anionic surface-active agents are composed of salts of fatty acids, such as oleic, ricinoleic, palmitic and stearic acids, coconut oil acid or hydrogenated coconut oil acid and in particular amine salts, such as amine stearates.

Mention may also be made of:

acyllactylates in which the acyl radical comprises from 8 to 20 carbon atoms, polyglycol ether carboxylic acids corresponding to the formula:

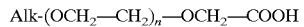

$$\text{Alk-}(OCH_2\text{—}CH_2)_n\text{—}OCH_2\text{—}COOH$$

in the acid or salified form, where the substituent Alk corresponds to a linear chain having from 12 to 18 carbon atoms and where n is an integer of between 5 and 15.

Mention may be made, among non-ionic surfactants which can be used alone or as a mixture, of in particular: polyethoxylated, polypropoxylated or polyglycerolated alcohols, alkylphenols and fatty acids with a fatty chain containing 8 to 18 carbon atoms. Mention may also be made of copolymers of ethylene oxide and of propylene oxide, condensates of ethylene and propylene oxide with fatty alcohols, polyethoxylated fatty amides, polyethoxylated fatty amines, ethanolamides, fatty acid esters of glycol, optionally oxyethylenated fatty acid esters of sorbitan, fatty acid esters of sucrose, fatty acid esters of polyethylene glycol, phosphoric triesters or fatty acid esters of glucose derivatives.

Other compounds which come within this classification are condensation products of an α-diol, of a monoalcohol, of an alkylphenol, of an amide or of a diglycolamide with glycidol or a glycidol precursor.

The non-ionic surfactants which are mainly used are polyethoxylated or polyglycerolated alcohols, such as polyethoxylated stearyl, cetylstearyl and oleyl alcohols.

The preferentially used anionic surfactants are amine stearates.

The compositions according to the invention can also be provided in the form of a gel, of an aqueous or aqueous/alcoholic solution of one or a number of water-soluble polymers, such as polyacrylic acid derivatives, or in the form of emulsified gels obtained by dispersion of oils in gels using emulsifiers such as Pemulens® from the Company Goodrich.

The compositions according to the present invention can additionally contain standard ingredients chosen from softeners, preservatives, sequestering agents, fragrances, thickeners, cohesion agents or polymers, as well as basifying or acidifying agents, moisturizing agents and water-soluble active principles.

The thickeners which can be used may be natural or synthetic. Mention may be made, among natural thickeners, of gums of various sorts, such as gum arabic, guar gum or locust bean gum. Mention may be made, among synthetic thickeners, of cellulose derivatives, such as hydroxyethyl cellulose or carboxymethyl cellulose, starch derivatives, cellulose ether derivatives possessing quaternary ammonium groups, cationic polysaccharides, salts of acrylic or methacrylic polymers, polyenes or polysiloxanes.

It is also possible to obtain a thickening of the compositions by mixing polyethylene glycol and polyethylene glycol stearate and/or distearate or with a mixture of phosphoric esters and of fatty amides.

According to the invention, the oily phase can represent from 0.1 to 50% by weight with respect to the total weight of the emulsion.

It can be composed of oils and/or of waxes.

The waxes and the oils can be of vegetable, animal, mineral or synthetic origin.

Mention may be made, among the vegetable oils, of jojoba oil, olive oil, sweet almond oil, avocado oil, coconut oil, wheatgerm oil, maize oil, palm oil, sesame oil, soybean oil, argan oil, evening primrose oil, borage oil and essential oils.

Mention may in particular be made, among animal oils, of fish oil.

Mention may be made, among mineral oils, of liquid paraffin and of isohexadecane.

Mention may be made, among synthetic oils, of ethyl and isopropyl palmitates, 2-ethylhexyl palmitate, alkyl myristates, such as isopropyl, butyl or cetyl myristate, hexyl stearate, triglycerides of octanoic and decanoic acids, cetyl ricinoleate and stearyl octanoate, silicone oils, perfluorinated oils or fluorinated silicone oils.

The oily phase can moreover contain dyes, sunscreen agents, antioxidants, preservatives and lipophilic active principles.

According to the invention, the anhydrous compositions which can be provided in the loose or compact powder or solid, pasty or liquid make-up form can contain a binder which can preferably represent from 0.01 to 95% by weight with respect to the total weight of the composition.

Mention may in particular be made, among binding agents, of animal, vegetable or synthetic oils or mixtures of oil(s) and wax(es) and in particular mink oil, turtle oil, soybean oil, grape seed oil, sesame oil, maize oil, rapeseed oil, sunflower oil, cottonseed oil, avocado oil, olive oil, castor oil, jojoba oil, groundnut oil, and the like; hydrocarbon oils, such as liquid paraffins, squalane, petrolatum, and the like; esters, such as isopropyl myristate, isopropyl palmitate, butyl stearate, hexyl laurate, isononyl isononanate, 2-ethylhexyl palmitate, 2-hexyldecyl laurate, 2-octyldecyl palmitate, 2-octyidodecyl myristate, di(2-ethylhexyl) succinate, diisostearyl malate, 2-octyldodecyl lactate, glycerol triisostearate, diglycerol triisostearate, and the like; silicone oils, such as polymethylsiloxanes, polymethylphenylsiloxanes, polysiloxanes modified by fatty acids, polysiloxanes modified by fatty alcohols, polysiloxanes modified by polyoxyalkylenes, fluorinated silicones, and the like; perfluorinated and/or organofluornated oils; higher fatty acids, such as myristic acid, palmitic acid, stearic acid, behenic acid, oleic acid, linoleic acid, linolenic acid, isostearic acid, and the like; higher fatty alcohols, such as cetanol, stearyl alcohol, oleyl alcohol and the like; the waxes can be chosen in particular from carnauba wax, candelilla wax, beeswax, whale wax, lanolins, microcrystalline waxes, and the like.

The binder can additionally contain volatile oils, which will evaporate on contact with the skin but the presence of which in the cosmetic composition is useful because they facilitate spreading of the composition during application on the skin. Such spreading agents, known here as "volatile oils", are generally oils having, at 25° C., a saturated vapour pressure of at least 0.5 millibar (i.e. 50 Pa).

Mention will be made, among the volatile oils which can be present as spreading agents in the composition of the invention, for example, of silicone oils, such as hexamethyldisiloxane, cyclopentadimethylsiloxane or cyclotetramethylsiloxane, fluorinated oils, such as that sold under the name Galden® (Montefluos), or isoparaffin oils, such as those sold under the name Isopar® (E, G, L or H; Exxon Chemical).

As mentioned above, the compositions according to the invention can also be provided in the form of an anhydrous or aqueous nail varnish.

When the compositions are provided in the form of an anhydrous nail varnish, the solvent system represents approximately from 55% to 90% by weight with respect to the total weight of the varnish.

This solvent system is composed of a mixture of various volatile organic solvents, such as acetone, ethyl acetate, butyl acetate, 2-methoxyethyl acetate, methyl ethyl ketone, methyl isobutyl ketone, methyl acetate, amyl acetate and isopropyl acetate.

The solvent system can also comprise a diluent, such as hexane or octane or alternatively an aromatic hydrocarbon, such as toluene or xylene, in a proportion of 10 to 35% by weight with respect to the total weight of the varnish.

The film-forming material of the varnish is generally present at a concentration of between 5 and 20% by weight with respect to the total weight of the varnish.

Mention may in particular be made, among film-forming materials, of nitrocelluloses of the "RS" or "SS" type and in particular type 1/4"RS" nitrocellulose, type 1/2"RS" nitrocellulose, type 1/2"SS" nitrocellulose and type 3/4"RS" nitrocellulose. The varnishes also contain a plasticizing agent generally present at a concentration of between 2 and 10% by weight with respect to the total weight of the varnish. Mention may in particular be made, among these, of tricresyl phosphate, benzyl benzoate, triethyl citrate, tributyl citrate, triethyl acetylcitrate, tri(2-ethylhexyl)acetylcitrate, diamyl phthalate or camphor.

The varnishes according to the invention also contain a resin generally present at a concentration of between 0.5 and 15% by weight with respect to the total weight of the varnish.

Mention may in particular be made, among the numerous resins which can be used, of resins of the arylsulphonamide-formaldehyde or arylsulphonamide-epoxy type, in particular the resins known under the trade names Santolite MHP® and Santolite MS 80%.

When the nail varnishes are provided in the aqueous form, they contain a dispersion of a synthetic film-forming substance to which various standard additives can be added, such as a film-forming material, a thickener, a pH regulator, a crosslinking agent, an antifoaming agent, and the like.

It is possible, as synthetic aqueous dispersion, inter alia, to use dispersions of poly(vinyl acetate), of polyurethane, of acrylic polymers or copolymers and of copolymers of poly(vinyl acetate).

According to the invention, the synthetic aqueous dispersion represents approximately from 10 to 80% by weight of the varnish.

The film-forming material is generally present in a concentration of between 5 and 20% by weight with respect to the total weight of the varnish. Mention may in particular be made, among the film-forming materials, of water-soluble cellulose derivatives.

The varnishes according to the invention can also contain a resin generally present at a concentration of between 0.5 and 15% by weight with respect to the total weight of the varnish.

Mention may in particular be made, among the resins which can be used, of resins of the acrylic, styrene, acrylate-styrene and vinyl type.

The anhydrous or aqueous nail varnishes according to the invention can also contain adjuvants commonly used in nail varnishes, such as, for example, U.V. screening agents.

The examples hereinbelow make it possible to illustrate the different colour effects obtained with different LC pigments in the compositions according to the invention. The percentages of the constituents of the compositions are expressed by weight, the sum of all the constituents being equal to 100.

EXAMPLE 1
Clear Aqueous Nail Varnish

| Component | % |
| --- | --- |
| Aqueous polyurethane dispersion, Solids content: 34% Sancure | 94.50 |
| Spreading agent | 0.50 |
| LC pigment | 5.00 |
| Nitrocellulose | 10.820 |
| Toluenesulphonamide-formaldehyde resin, "Ket Jenflex MS 80", Akzo | 10.740 |
| Tributyl acetylcitrate, "Citroflex A4", Pfizer | 6.495 |
| Toluene | 30.910 |
| Butyl acetate | 20.640 |
| Ethyl acetate | 9.270 |
| sopropanol | 7.720 |
| LC pigment | 2.000 |
| Citric acid | 0.055 |

The varnish obtained was iridescent white in the bottle.

On applying the nail varnishes according to the invention directly on the nail, a slight coloured effect was obtained in the tones of the colour pair of the pigment employed.

On applying the nail varnish according to the invention with the pigment SLM 41101 on a black varnish base, an intense colour was obtained which changes from blue to green according to the angle of observation (or the inclination of the nail). The same effect was found for the specific colours of the pigments SLM 41102 and SLM 41103.

On applying the nail varnish according to the invention with the pigment SLM 41102 on a red varnish base, a novel orangey colour was obtained with red and gold highlights.

An effect with similar colours was found for a varnish comprising, in the same composition, an LC pigment in combination with one or a number of other standard pigments.

EXAMPLE 2
Transparent Mascara

| Component | % |
| --- | --- |
| Stearic acid | 6.00 |
| Glyceryl stearate | 3.70 |
| Beeswax | 5.50 |
| Carnauba wax | 1.90 |
| Paraffin | 7.50 |
| Rosin | 1.80 |
| Ethylparaben | 0.04 |
| Propylparaben | 0.03 |
| LC pigment | 5.00 |
| Methyiparaben | 0.23 |
| Triethanolamine | 3.00 |
| Hydroxyethyl cellulose | 0.20 |
| Ethoxydiglycol | 0.02 |
| Acacia | 5.80 |
| Water | q.s. for100 |

A product was obtained which is iridescent white in the bottle.

When the composition according to the invention was applied with the pigment SLM 41101 directly on black eyelashes, a very intense green make-up was obtained which became blue according to the angle of observation. The same effect was found for the specific colours of the pigments SLM 41102 and SLM 41103.

When the composition according to the invention was applied on a black mascara base, the same effect was obtained but with more intense colours.

EXAMPLE 3
Blue Mascara

| Component | % |
| --- | --- |
| Stearic acid | 6.00 |
| Glyceryl stearate | 3.70 |
| Beeswax | 5.50 |
| Carnauba wax | 1.90 |
| Paraffin | 7.50 |
| Rosin | 1.80 |
| Ethylparaben | 0.04 |
| Propylparaben | 0.03 |
| Ultramarine blue | 6.10 |
| Ultramarines and silica | 0.90 |
| Titanium dioxide | 0.50 |
| LC pigment | 5.00 |
| Methylparaben | 0.23 |
| Triethanolamine | 3.00 |
| Hydroxyethyl cellulose | 0.20 |
| Ethoxydiglycol | 0.02 |
| Acacia | 5.80 |
| Water | q.s. for100 |

The colour of the mascara in the bottle was more intense and luminous than the same mascara in the absence of LC pigment (control). With the pigment SLM 41101, the composition attained green-blue and gold highlights.

When the composition according to the invention was applied on the eyelashes, a more intense blue colouring was obtained than with the control. Moreover, the makeup became green according to the angle of observation.

EXAMPLE 4
Oil-in-water Emulsion Face Cream

| Component | % |
|---|---|
| Stearic acid | 2.00 |
| Glyceryl stearate | 3.00 |
| Glyceryl isostearate | 2.00 |
| Mineral oil | 8.00 |
| Propylparaben | 0.21 |
| Dimethicone | 4.00 |
| LC pigment | 5.00 |
| Triethanolamine | |
| Methylparaben | 0.20 |
| 5% Magnesium aluminium silicate gel | 20.00 |
| Cellulose gum | 3.50 |
| Sodium lauroylsarcosinate | 3.50 |
| Glycerol | 2.00 |
| Diazolidinylurea | 0.30 |
| Water | q.s. for100 |

A white cream with iridescent highlights was obtained.

When the composition according to the invention was applied on the back of the hand, a very luminous, slightly glittery effect with coloured highlights was obtained. When the composition according to the invention comprising the LC pigment SLM 41102 was applied on a red lipstick base, a brighter colour with gold highlights was obtained. An effect with similar colours was found for a lipstick comprising, in the same composition, an LC pigment in combination with one or a number of other standard pigments.

What is claimed is:

1. A cosmetic composition comprising a cosmetically acceptable vehicle and a liquid crystal (LC) coloring agent in an amount capable of producing a color within a range of hues, said color existing between at least two specific colors and varying as a function of the incidence of the light and the angle of observation, said coloring agent being chosen from linear or cyclic polymers onto which are grafted mesomorphic groups, and said LC coloring agent being used in combination with at least one non-LC coloring agent, wherein said cosmetically acceptable vehicle is present in an amount cosmetically effective for making up the nails, wherein said composition is an aqueous or anhydrous nail enamel, wherein the total amount of said LC coloring agent and said at least one non-LC coloring agent ranges from about 0.01 and about 60% by weight with respect to the total weight of the composition, and wherein the ratio of said LC coloring agent to said at least one non-LC coloring agent ranges from about 20/1 to about 1/20.

2. A cosmetic composition comprising a cosmetically acceptable vehicle and a liquid crystal (LC) coloring agent in an amount capable of producing a color within a range of hues, said color existing between at least two specific colors and varying as a function of the incidence of the light and the angle of observation, said coloring agent being chosen from linear or cyclic polymers onto which are grafted mesomorphic groups, and said LC coloring agent being used alone or in combination with at least one non-LC coloring agent, wherein said cosmetically acceptable vehicle and said coloring agent are present in an amount cosmetically effective for making up the skin, lips, nails, hair, or eyelashes, and wherein said composition contains at least one black coloring agent.

3. A composition according to claim 1, wherein the LC coloring agent is chosen from silicones and cellulose ethers onto which are grafted mesomorphic groups.

4. A composition according to claim 2, wherein the LC coloring agent is chosen from silicones and cellulose ethers onto which are grafted mesomorphic groups.

5. A composition according to claim 1, wherein the LC coloring agent is in the form of an amorphous white powder having a color and/or coloring effect, wherein said color and/or coloring effect only appears upon spreading the composition onto a substrate.

6. A composition according to claim 2, wherein the LC coloring agent is in the form of an amorphous white powder having a color and/or coloring effect, wherein said color and/or coloring effect only appears upon spreading the composition onto a substrate.

7. A composition according to claim 1, wherein the LC coloring agent is in the form of a powder, wherein said LC coloring agent comprises a mesomorphic group comprising oriented substances with three-dimensional crosslinking, and wherein said LC coloring agent has a mean thickness ranging from 1 to 100 pm and a mean diameter ranging from 1 to 10,000 µm.

8. A composition according to claim 3, wherein the LC coloring agent is in the form of a powder, wherein said LC coloring agent comprising a mesomorphic group comprising oriented substances with three-dimensional crosslinking, and wherein said LC coloring agent has a mean thickness ranging from 1 to 100 pm and a mean diameter ranging from 1 to 10,000 µm.

9. A composition according to claim 1, wherein the LC coloring agent is chosen from cyclic polyorganosiloxanes grafted with cholesterol and biphenyl groups.

10. A composition according to claim 2, wherein the LC coloring agent is chosen from cyclic polyorganosiloxanes grafted with cholesterol and biphenyl group.

11. A composition according to claim 2, wherein the total amount of LC and non-LC coloring agents, when the composition also contains non-LC coloring agents, ranges from about 0.01 to about 60% by weight with respect to the total weight of the composition.

12. A composition according to claim 1, wherein the total amount of LC and non-LC coloring agents ranges from about 0.1 to about 30% by weight with respect to the total weight of the composition.

13. A composition according to claim 2, wherein the total amount of LC and non-LC coloring agents ranges from about 0.1 to about 30% by weight with respect to the total weight of the composition.

14. A composition according to claim 1, wherein the total amount of LC and non-LC coloring agents ranges from about 1 to about 20% by weight with respect to the total weight of the composition.

15. A composition according to claim 2, wherein the total amount of LC and non-LC coloring agents ranges from about 1 to about 20% by weight with respect to the total weight of the composition.

16. A composition according to claim 2, wherein the ratio of the LC coloring agents to the non-LC coloring agents by weight ranges from about 20/1 to about 1/20.

17. A composition according to claim 1, wherein the ratio of the LC coloring agents to the non-LC coloring agents by weight ranges from about 10/1 to about 1/10.

18. A composition according to claim 2, wherein the ratio of the LC coloring agents to the non-LC coloring agents by weight ranges from about 10/1 to about 1/10.

19. A composition according claim 1, wherein the ratio of the LC coloring agents to the non-LC coloring agents by weight ranges from about 5/1 to about 1/5.

20. A composition according claim 2, wherein the ratio of the LC coloring agents to the non-LC coloring agents by weight ranges from about 5/1 to about 1/5.

21. A composition according to claim 1, wherein said composition contains from about 0.01 to about 90% by weight of fillers with respect to the total weight of the composition.

22. A composition according to claims 2, wherein said composition contains from about 0.01 to about 90% by weight of fillers with respect to the total weight of the composition.

23. A composition according to claim 1, wherein said composition is an oil-in-water or water-in-oil emulsion, a suspension in solvent medium, an anhydrous paste, or is in gel form.

24. A composition according to claim 2, wherein said composition is an oil-in-water or water-in-oil emulsion, a suspension in solvent medium, a loose powder or a compact powder, an anhydrous solid or an anhydrous paste, or is in gel or mousse form.

25. A composition according to claim 1, wherein the color of said non-LC coloring agent substantially corresponds to one of the specific colors of the LC coloring agent.

26. A composition according to claim 2, wherein said composition comprises at least one non-LC coloring agent, and wherein the color of said non-LC coloring agent substantially corresponds to one of the specific colors of the LC coloring agent.

27. A cosmetic composition according to claim 1, wherein the color of said non-LC coloring agent is different from the specific colors of the LC coloring agent.

28. A cosmetic composition according to claim 2, wherein said composition comprises at least one non-LC coloring agent, and wherein the color of said non-LC coloring agent is different from the specific colors of the LC coloring agent.

29. A cosmetic composition according to claim 11, wherein said composition comprises at least one black coloring agent.

30. A method for treating a surface to reinforce the color thereof, comprising applying to the surface a cosmetic composition as defined in claim 26.

31. A method for treating the skin or lips to reinforce the color thereof, comprising applying to the surface a cosmetic composition as defined in claim 26.

32. A method for modulating the color of a surface, comprising applying to the surface a cosmetic composition as defined in claim 27.

33. A method for modulating the color of the nails, comprising applying to the surface a cosmetic composition as defined in claim 27.

34. A method for modulating the color of a surface, comprising applying to the surface a cosmetic composition as defined in claim 28.

35. A method for modulating the color of the skin or lips, comprising applying to the surface a cosmetic composition as defined in claim 2.

36. A composition according to claim 1, wherein said LC coloring agent is a silicone or cellulose ether, onto which is grafted at least one mesomorphic group of formula

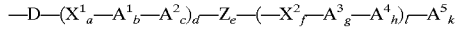

in which

D represents a $C_1$–$C_{20}$ alkylene residue, optionally substituted by one or a number of halogens, for which one or a number of the non-neighboring methylene units can be replaced by an $X^1$ group, $X^1$ and $X^2$ independently represent —O—, —COO—, —CONH—, —CO—, —S—, —C≡C—, —CH=CH—, —CH$_2$—CH$_2$—, —CH=N—, —N=N— or —N=N(O)— divalent radicals, $A^1$, $A^2$, $A^3$ and $A^4$ independently represent optionally substituted 1,4-phenylene, 1,4-cyclohexylene, arylene, heteroarylene or cycloalkylene divalent radicals, Z independently represents divalent to tetravalent radicals, benzene-1,4-cyclohexane or benzene-1,3-cyclopentane, $A^5$ independently represents a -5-saturated or unsaturated alkyl, alkoxy or cycloalkyl radical having 1 to 16 carbon atoms, a steroidal radical, a halogen, a hydrogen atom or a hydroxyl, nitrile or trialkylsilyloxy radical, a,b,c,d,f,g,h,l and k independently represent an integer ranging from 0 to 3, e represents 0 or 1, wherein the sum a+b+c+d+e+f+g+h+l+k+ is greater than or equal to 2 and the sum d+l is less than or equal to 4, and wherein the mesomorphic groups do not comprise a peroxide radical.

37. A composition according to claim 2, wherein said LC coloring agent is a silicone or cellulose ether, onto which is grafted at least one mesomorphic group of formula

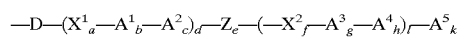

in which

D represents a $C_1$–$C_{20}$ alkylene residue, optionally substituted by one or a number of halogens, for which one or a number of the non-neighboring methylene units can be replaced by an $X^1$ group, $X^1$ and $X^2$ independently represent —O—, —COO—, —CONH—, —CO—, —S—, —C≡C—, —CH=CH—, —CH$_2$—CH$_2$—, —CH=N—, —N=N— or —N=N(O)— divalent radicals, $A^1$, $A^2$, $A^3$ and $A^4$ independently represent optionally substituted 1,4-phenylene, 1,4-cyclohexylene, arylene, heteroarylene or cycloalkylene divalent radicals, Z independently represents divalent to tetravalent radicals, benzene-1,4-cyclohexane or benzene-1,3-cyclopentane, $A^5$ independently represents a -5-saturated or unsaturated alkyl, alkoxy or cycloalkyl radical having 1 to 16 carbon atoms, a steroidal radical, a halogen, a hydrogen atom or a hydroxyl, nitrile or trialkylsilyloxy radical, a,b,c,d,f,g,h,l and k independently represent an integer ranging from 0 to 3, e represents 0 or 1, wherein the sum a+b+c+d+e+f+g+h+l+k+ is greater than or equal to 2 and the sum d+l is less than or equal to 4, and wherein the mesomorphic groups do not comprise a peroxide radical.

* * * * *

UNITED STATES PATENT AND TRADEMARK OFFICE
CERTIFICATE OF CORRECTION

PATENT NO.    : 6,346,237 B2
DATED         : February 12, 2002
INVENTOR(S)   : Lemann et al.

It is certified that error appears in the above-identified patent and that said Letters Patent is hereby corrected as shown below:

Column 14,
Line 15, "100 pm" should read -- 100 $\mu$m --.
Line 17, "claim 3" should read -- claim 2 --.
Line 22, "100 pm" should read -- 100 $\mu$m --.
Line 28, "group" should read -- groups --
Line 58, "according claim" should read -- according to claim --.
Line 61, "according claim" should read -- according to claim --.

Column 15,
Line 1, "claims" should read -- claim --.
Line 29, "claim 11" should read -- claim 1 --.
Line 49, "claim 2" should read -- claim 28 --.

Column 16,
Line 21, "a+b+c+d+e+f+g+h+l+k+" should read -- a+b+c+d+e+f+g+h+l+k --.
Line 53, "a+b+c+d+e+f+g+h+l+k+" should read -- a+b+c+d+e+f+g+h+l+k --.

Signed and Sealed this

Eighth Day of October, 2002

*Attest:*

JAMES E. ROGAN
*Attesting Officer*          *Director of the United States Patent and Trademark Office*